United States Patent [19]
Monshipouri et al.

[11] Patent Number: 5,626,870
[45] Date of Patent: May 6, 1997

[54] METHOD OF FORMING HYDROGEL PARTICLES HAVING A CONTROLLED SIZE USING LIPOSOMES

[75] Inventors: Mariam Monshipouri, Bethesda; Alan S. Rudolph, Bowie, both of Md.

[73] Assignee: Georgetown University, Washington, D.C.

[21] Appl. No.: 556,849

[22] Filed: Nov. 2, 1995

Related U.S. Application Data

[62] Division of Ser. No. 152,366, Nov. 16, 1993, Pat. No. 5,464,629.

[51] Int. Cl.$^6$ .......................... A61K 9/127; B01J 13/02
[52] U.S. Cl. .......................... 424/450; 424/489; 424/490; 424/493; 424/496; 424/499; 424/500; 428/402.2; 264/4.1; 264/4.3; 514/54
[58] Field of Search ............ 424/450, 489–501; 428/402.2; 264/4.1, 4.3; 514/54

[56] References Cited

U.S. PATENT DOCUMENTS

| | | | |
|---|---|---|---|
| 4,192,900 | 3/1980 | Cheng | 426/579 |
| 4,520,178 | 5/1985 | Sakata | 526/200 |
| 4,839,111 | 6/1989 | Huang | 264/4.6 |
| 5,104,736 | 4/1992 | Wallach | 428/402.2 |

*Primary Examiner*—Gollamudi S. Kishore
*Attorney, Agent, or Firm*—Oblon, Spivak, McClelland, Maier & Neustadt, P.C.

[57] ABSTRACT

A method of fabricating hydrogel particles within liposomes, which entails: a) encapsulating an effective amount of each of one or more hydrogel substances and one or more release agents in liposomes in a liquid medium, b) removing any unencapsulated hydrogel substances and release agents from the liquid medium, c) adding initiator to the liquid medium and into the liposomes, thereby initiating reaction of the one or more hydrogel substances, whereby hydrogel particles are formed in the liposomes, and d) removing any extra-liposomal initiator from the medium.

10 Claims, 2 Drawing Sheets

METHOD OF FORMING HYDROGEL PARTICLES HAVING A CONTROLLED SIZE USING LIPOSOMES

This is a Division, of application Ser. No. 08/152,366 filed on Nov. 16, 1993, now U.S. Pat. No. 5,464,629

BACKGROUND OF THE INVENTION

1. Field of the Invention

The present invention relates to a method for fabricating hydrogel particles having an accurately controlled size using liposomes.

2. Description of the Background

Liposomes may be generally defined as closed vesicles having a lipid membrane surrounding an entrapped aqueous core. They may be either unilamellar vesicles having a single membrane layer or multilamellar vesicles having multiple membrane layers.

Liposomes have been used in a variety of commercial applications, and for encapsulating a variety of different agents therein. For example, liposomes have been used as a delivery vehicle for the sustained release of drugs both in parental and topical applications. It is known that liposomes may be targeted to specific cells in the body when used in association with immunoglobulins raised against the target cells.

Liposomes have been fabricated using a number of different lipid formulations and methods depending upon the specific intended use. Further, methods are known for producing liposomes of a particular size and wall thickness. For example, such methods have included the use of hydrodynamic shear, U.S. Pat. No. 5,082,664, reverse phase evaporation, U.S. Pat. No. 4,235,571, sonication, U.S. Pat. No. 4,089,801, detergent dialysis and extrusion through a membrane pores, U.S. Pat. No. 5,008,050. In these methods, the lipid compositions used are chosen based upon properties related to solution dynamics, such as aggregation and fusion, or controlled release, such as release of encapsulated agents.

Hydrogels are polymers which contain chemical constituents having a high water content and high viscosity. These materials are used, for example, as fillers in the food industry, as biomaterials for use in contact lens material and as controlled release matrices, for example. One example is cross-linked polyethylene oxide which absorbs up to 100 times its weight of water, which can be released when desired. Another example of a hydrogel is the alginates, which are high molecular weight oligosaccharides derived from algae. At present, alginate hydrogel particles are fabricated using methods which involve drops formed as an alginate solution is extruded from a needle or sprayed from a nozzle. These generally result in particles having a size range of from 0.5 to 10 mm. Unfortunately, however, it is presently difficult to accurately control the size of such particles in large scale. For example, both of U.S. Pat. Nos. 4,520,178 and 4,192,900 describe methods of producing hydrogel particles, but neither of the methods described therein afford hydrogel particles in the submicron range with the same unimodal distribution of size. Also, neither of these methods affords particles which are surrounded by a lipid bilayer. Thus, although hydrogel reactions in liposomes have been conducted, the particles formed are not formed in liposomes of unimodal submicron size, nor do they involve hydrogel reactions which rely on transporting the initiator of the reaction across the liposome bilayer.

It would be extremely desirable, however, if a method for fabricating hydrogel particles were known wherein very accurate control of the hydrogel particle size could be obtained. This would allow for the release of chemicals, drugs or other materials therefrom in a very controlled manner.

SUMMARY OF THE INVENTION

Accordingly, it is an object of the present invention to provide a method for fabricating hydrogel particles wherein accurate control of the hydrogel particle size is obtained.

It is also an object of the present invention to provide a method for fabricating hydrogel particles within the aqueous compartment of liposomes.

It is further an object of the present invention to provide a method for accurately controlling the formation of hydrogel particles by controlling the liposome size used for the gelation reaction.

The above objects and others are provided by a method for forming hydrogel particles within the aqueous compartment of bilayered liposomes, which entails:

a) encapsulating an effective amount of each of one or more hydrogel substances in bilayered liposomes in a liquid medium, b) removing any unencapsulated hydrogel substances agents from the medium, c) adding an initiator to the medium and into the liposomes through the lipid bilayer into the liposomes, thereby initiating reaction of the one or more hydrogel substances, whereby hydrogel particles are formed in the aqueous compartment of the liposomes, and d) removing any remaining extra-liposomal initiator from the medium.

DETAILED DESCRIPTION OF THE PREFERRED EMBODIMENTS

Figure 1:
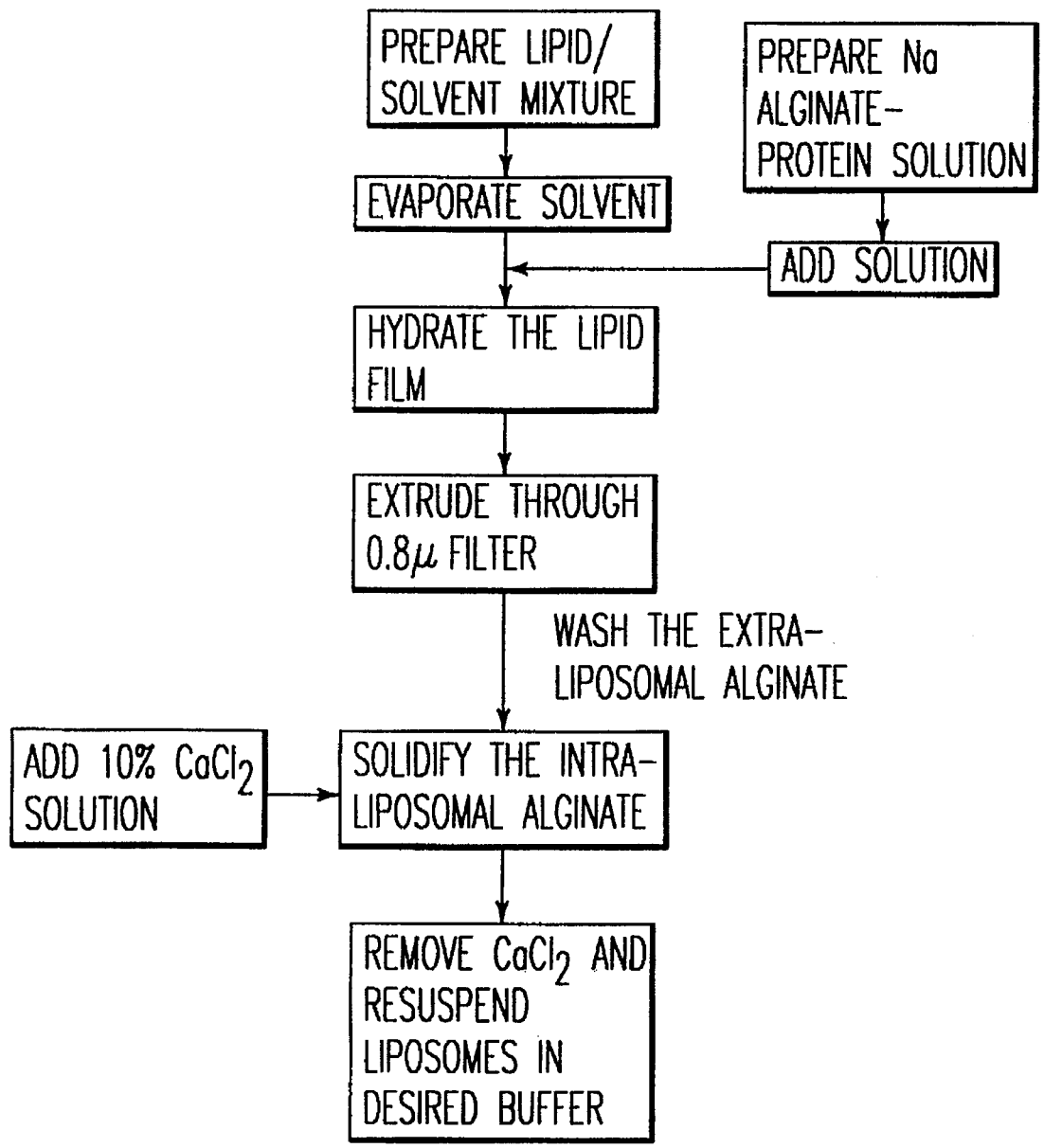
FIG. 1 is a flow diagram of the present process by which liposome encapsulated hydrogel particles are fabricated.
Figure 2:
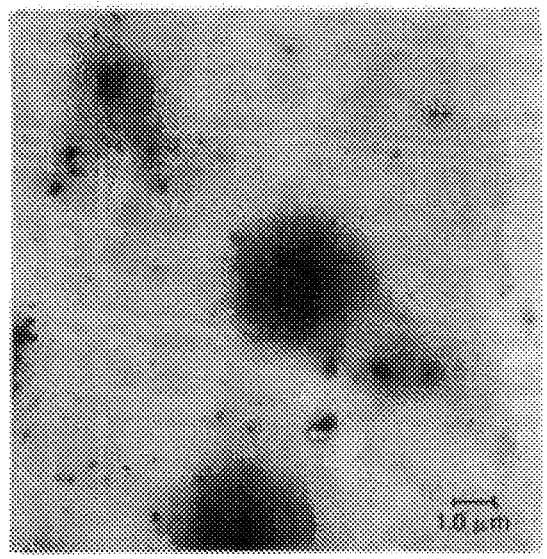
FIG. 2 is an electron micrograph of the formed particles of the present invention.
Figure 3:
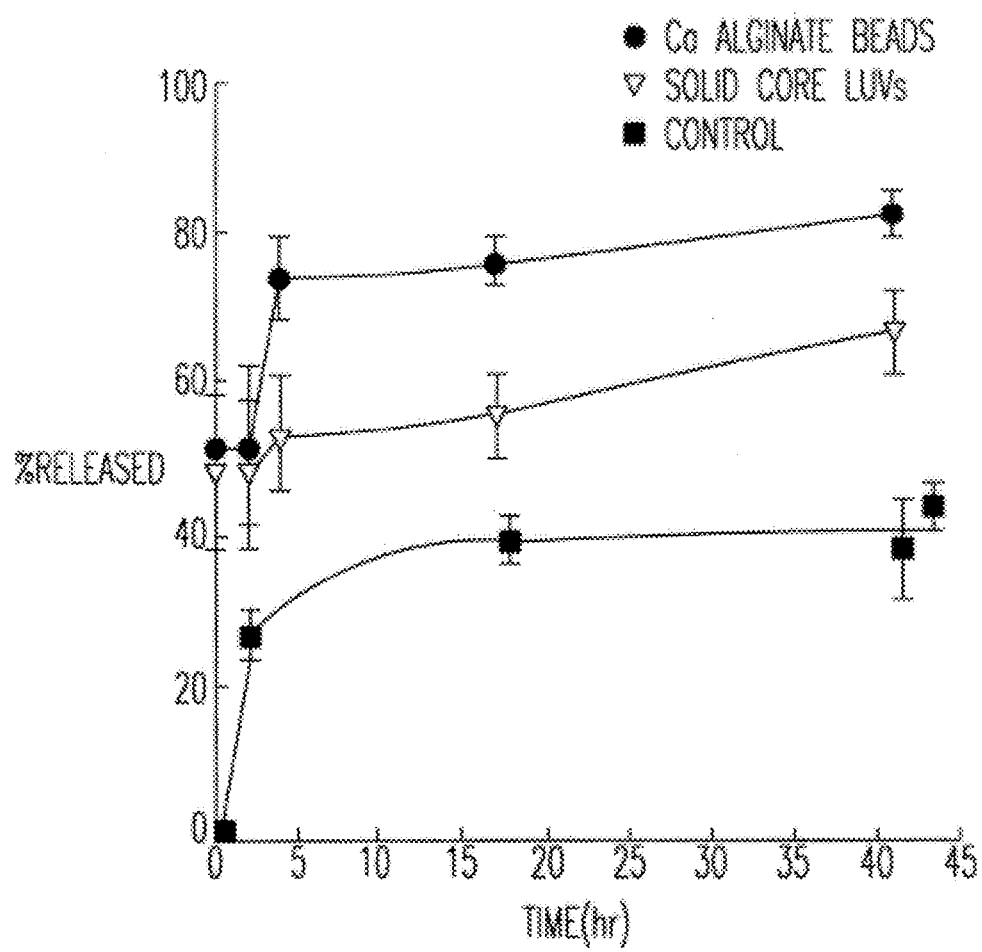
FIG. 3 is a controlled release profile of hydrogel particles formed from inside a liposome with and without the lipid bilayer surrounding the hydrogel particle.

In accordance with the present invention, it has been surprisingly discovered that hydrogel particles can be formed within the aqueous compartment of bilayered liposomes to accurately control the size of the hydrogel particles formed. Generally, in accordance with this invention, the fabrication of hydrogel particles within liposomes entails encapsulating an effective amount of each of one or more hydrogel substances and, further, one or more active agents, and permeating an initiator across the lipid bilayer to effect gelation or cross-linking of the one or more hydrogel substances in the aqueous compartment of the liposome. The lipid bilayer is then removed to afford accurately sized hydrogel particles for controlled release of whatever active agent is encapsulated therein.

A wide variety of hydrogel substances or types may be used in accordance with the present invention. For example, chitosan, K-carrageenan or sodium or calcium alginate may be used. However, these are only examples and any other hydrogel substances or types known to those skilled in the art may also be used.

In general, the encapsulation of the hydrogel substances and the desired active agent therein may be effected by any conventional method of liposome fabrication, such as, for example, sonication and hydrodynamic shear. The composition of the lipids used in the fabrication of liposomes may be varied as long as the result is a stable liposome that does not readily fuse or aggregate in solution.

Generally, any lipid composition may be used as long as it affords stable liposomes. For example, phosphatidylcholine and cholesterol may be used in combination with either phosphatidylserine or dicetylphosphate. Alternatively, dipalmitoyl phosphatidylcholine may be used. However, these are only examples and the liposomes may be prepared from a wide variety of lipid materials including phosphatidyl ethers and esters, phosphatidyl ethanolamine, phosphatidylcholine, glycerides, cerebrosides, gangliosides, sphingomycelin, steroids and cholesterol. In general, U.S. Pat. No. 4,235,871 is noted, which is incorporated herein in the entirety. Further, in general, any liposome-forming lipid may be used in accordance with the present invention.

U.S. Pat. Nos. 4,089,801; 4,235,571; 5,082,664 and 5,008,050 are incorporated herein in their entirety.

Once the liposomes are formed containing therein the one or more encapsulated hydrogel substances and the one or more desired active agents, any unencapsulated hydrogel substances and active agents may be removed by any conventional separation method used in liposome fabrication, which includes, for example, centrifugation, filtration and column chromatography. These methods are well known to those skilled in the art.

Further, a transport agent is added to the bulk solution after encapsulation of the soluble hydrogel monomer in the interior core of the liposomes and removal of extraliposomal hydrogel monomer. In accordance with the present invention, the use of a transport agent is important for effecting gelation of the interior core of the liposomes.

In general, an "effective amount" of transport agent is used, which amount varies depending upon the nature of the gelation reaction of interest. Generally, however, this amount is about 7% of the concentration of soluble hydrogel (0.5% wt./vol) in order to effect couple to gelation. This correspond to about 0.035% wt/vol of transport agent, i.e. calcium ion.

In accordance with the present invention, any one or more transport agents may be used that are effective to transport one or more crosslinking agents across the lipid bilayer. Non-limitative examples thereof are sodium pectate, tragacanth gum, locust bean gum, PVA or PHEMA, for example.

Initiation of the reaction which results in the formation of the hydrogel particles within the liposome requires the addition of an initiator into the liposome compartment. Depending on the nature of one or more hydrogel substances, the initiator may be an ion or any other chemical or physical initiator of hydrogel reactions. The introduction of the initiator to the liposome compartment may be effected by passive diffusion across the lipid bilayer, through an ion specific pore in the lipid bilayer, or by active transport through a protein channel embedded in the lipid bilayer.

After introducing the initiator and forming the hydrogel particles within the liposome compartment, any remaining extra-liposomal initiator may be removed by any of the separation methods described above. The resulting liposome contains a lipid bilayer having the hydrogel particle within the aqueous compartment. Further, the lipid bilayer may be removed by detergent solubilization, if necessary.

The hydrogel particles formed in accordance with the present invention are extremely advantageous in a wide variety of utilities. As noted above, the present invention affords hydrogel particles having accurately controlled size characteristics, generally in the submicron range. For example, hydrogel particles may be used as controlled release matrices for the release of drugs, chemicals, antioxidants, enzymes and other biologically active compounds. Further, biological cells have also been encapsulated in hydrogels, such as alginate. Additionally, hydrogels have also been used as materials for the fabrication of biomaterials, such as contact lenses and as fillers in the food industry. The present invention is thus advantageous in view of all of these exemplary utilities.

Generally, the time periods required for each of steps a)–d) as described above are as follows. First, encapsulation step a) generally requires about 4 to 5 hours although shorter or longer times may be used. Second, removal of unencapsulated hydrogel monomers in step b) generally requires about 0.5 to 1 hour although shorter or longer times may be used. Third, formation of hydrogel particles in step c) generally depends upon the characteristics of the initiator and the type of liquid membrane, however, an exemplary time is on the order of about 2 hours although shorter or longer times may be used. Finally, removal of any extra-liposomal initiator in step d) generally requires about 0.5 hours although shorter or longer times may be used.

Further, sonication and hydrodynamic shear are typically used as methods of encapsulation, while centrifugation, filtration and chromatography are typically used as separation methods.

Moreover, other examples of initiators are ionophores and $H^+$ and $OH^-$ ions.

Generally, any one or more chemical initiators may be used which are of sufficient hydrophobic character to pass through the bilayer. Further, specific pores or channels are provided in the membrane for the initiator to pass.

In accordance with the present invention, a variety of substances may be encapsulated in the present hydrogel particles, however, it is particularly advantageous to encapsulate one or more proteins or peptides therein. For example, substances such as growth factors or peptide drugs may be encapsulated in the hydrogel particles.

Generally, in accordance with the present invention, any biologically active or chemical substance may be encapsulated in the hydrogel of the present invention. These encapsulated substances may be, for example, and are not limited to drugs, such as antibiotic drugs, anti-inflammatory drugs, anti-neoplastic drugs and cardiotonic drugs; vitamins, particularly, anti-oxidant vitamins, such as vitamins C and E; growth factors; enzymes; peptides, polypeptides; proteins; and oligonucleotides.

Further, it is noted that the antibiotics, growth factors, enzymes, peptides, polypeptides, proteins and oligonucleotides used in accordance with the present invention may be natural as well as synthetic in origin, either being manually or machine-synthesized or produced by recombinant DNA methodologies.

Non-limitative examples of substances which are advantageously encapsulated in the present hydrogel are hormones, such as insulin; growth factors, such as transforming growth factor; cytokines, such as members of the interleukin family and oligonucleotides, such as antisense agents.

The present invention will now be further illustrated by reference to certain examples which are provided solely for purposes of illustration and are not intended to be limitative.

EXAMPLES

Example 1

Liposome formation:

Lipids consistent with the formation of liposomes are added to an organic phase and the mixture is dried in a rotary evaporator at 55° C. In this example, dipalmitoyl phosphatidylcholine was used. The dry lipid mixture was hydrated with a solution of 0.5% sodium alginate, in ungelled form, in buffer with removed calcium. The concentration of lipid in this example was 10 mg/ml, but may be any concentration which is consistent with efficient liposome formation. The solution was incubated to effect a good hydration with little lipid remaining insoluble. Following hydration, the liposomes were processed through a size reduction apparatus, in this example, a high pressure extruder. The solution of lipid with alginate was extruded through a 1.0 µm polycarbonate filter, and then subjected to repeated step extrusion through successful smaller micron polycarbonate filters. The final filter was selected to be 0.8 µm. The solution of unilamellar liposomes was then rinsed of sodium alginate that did not encapsulate by centrifugation. After each centrifugation step, the resulting pellet was resuspended in fresh buffer.

Hydrogel particle formation:

The solution of liposomes with sodium alginate was incubated in a solution of $CaCl_2$ to effect the formation of gelled calcium alginate within the liposome. In this example, the solution was 1.0M $CaCl_2$. The incubation period was long enough to effect the exchange of sodium with calcium to result in gel formation. The incubation period depends upon the concentration of $CaCl_2$ and the lipid bilayer composition (permeability coefficient). In this example, the liposome solution was incubated overnight at 4° C. Following the incubation, the particles were collected by centrifugation. The aggregated liposomes were treated with a saturated solution of sodium citrate to redisperse the solid core liposomes.

Example 2

A dispersion of liposomes containing calcium alginate was prepared as described in Example 1. The solution was then treated with a detergent to remove the lipid bilayer surrounding the alginate particle. In this example, the detergent was octyl-beta-glucoside at a concentration of 30 mM. The detergent used may be any typical detergent used for solubilization of the lipid bilayer, such as triton X-100 or sodium dodecylsulfate. The liposomes containing alginate particles were incubated in 30 mM octyl-beta-glucoside for 30 minutes. The lipid detergent was removed from the alginate particles by centrifuging the particles. The alginate particle pellet was then resuspended in fresh buffer without detergent. This results in a suspension of alginate particles with similar size characteristics to the liposomes created as described in Example 1. The main difference in the particles created in this example is the extra processing to remove the lipid bilayer surrounding the alginate particle.

Example 3

A dispersion of liposomes containing alginate particles was created as described in Example 1. The solution of particles once dispersed in buffer was then concentrated by centrifugation. The alginate particle pellet was resuspended in a solution of sodium alginate. A concentrated solution of $CaCl_2$ was added which results in the formation of a calcium alginate gel surrounding the liposomes containing calcium alginate particles.

Example 4

A dispersion of liposomes containing alginate particles was created as described in Example 1. In this example, a biological agent that will be controlled release was added in the initial hydration step. The biological agent will be incorporated into the alginate particle in the liposome. The release of the biological agent into the buffer may be measured by assaying or measuring the absorbance of the buffer in which the alginate particles are suspended.

Further, in accordance with the present invention, many hydrogel substances may be used which may be gelled within the aqueous compartment of the liposome.

Additionally, in accordance with one aspect of the present invention, fabrication times of about 8 to 10 hours are used. However, in accordance with another aspect of the present invention, the fabrication times of the hydrogel particles may be reduced, if desired, by using calcium ionophores in the lipid membrane such that the permeability rate of calcium through the lipid membrane is increased.

As noted above, the present invention provides hydrogel particles having an accurately controlled size and of certain porosity and release profile. In general, 100% of the hydrogel particles fabricated in accordance with the present invention will have a size or diameter of about 0.05 to 3.0 µm.

As used herein, the term "LUV" is an abbreviated term for Large Unilamellar Liposomes. These liposomes are reduced in size by extruding large liposomes named Multilamellar liposomes (MLVs) of about 0.8 µm pore diameter at high pressure as shown in FIG. 1.

Example 5

Three individual runs of size distribution measurements of LUVs and calcium alginate particles were effected. The following results were obtained.

TABLE 1

Size distribution analysis of solid core LUVs and calcium alginate particles.

| Particles | Mean diameter (nm) | |
|---|---|---|
| | Individual run | Overall |
| Solid core LUVs | 862 (320) 962 (320) 709 (240) | 844 (320) |
| Ca alginate particles | 783 (320) 750 (200) 711 (240) | 748 (280) |

In the above Table, the first figure represents mean diameter, and the second figure represents standard deviation. Thus, for example "862" refers to mean diameter, while "320" refers to standard deviation. An important point to note is that by comparing the value of mean diameters to standard deviation, it may be seen that the LUVs are predominantly uniform in size.

Generally as used herein, the term "effective amount" for the one or more hydrogel substances means an amount effective to produce an amount of gelled hydrogel which is sufficient to encapsulate or entrap the active agent of interest. Also, as used herein, the term "effective amount" for the one or more active agents means an amount effective for whichever activity the active agent is intended to exhibit. For example, if the active agent is an anti-inflammatory compound or composition, the amount used will be an anti-inflammatorily effective amount per unit dosage of liposomes. Likewise, if the active agent is a vitamin, the amount used will be at least a recommended daily dosage thereof. With these guidelines, the precise amounts used will be within the skill of the artisan.

The present invention, thus, provides solid core liposomes which constitute a delivery vehicle for the release of active agents in a mammal, particularly a human. This delivery vehicle is surprisingly advantageous as it combines the targeting characteristics of liposomes and the controlled release characteristic of a hydrogel matrix.

Having described the present invention, it will now be apparent to one of ordinary skill in the art that many changes and modifications may be made to the above-described embodiment without departing from the spirit and scope of the present invention.

What is claimed as new and desired to be secured by Letters Patent of the United States is:

1. Hydrogel particles having a size of from about 0.05 µm to 3.0 µm, which are produced by a process, which comprises:
   a) encapsulating one or more hydrogel-forming substances in liposomes in a liquid medium, said hydrogel-forming substances being selected from the group consisting of sodium alginate, chitosan and K-carrageenan;
   b) removing any unencapsulated hydrogel-forming substances from the liquid medium by centrifugation, filtration or column chromatography;
   c) adding calcium ions, as an initiator, to the liquid medium, thereby initiating cross-linking of the hydrogel-forming substances; and
   d) removing any extra calcium ions from the liquid medium by centrifugation, filtration or column chromatograph.

2. The hydrogel particles of claim 1, which further comprise one or more entrapped substances therein selected from the group consisting of drugs, vitamins, growth factors, hormones, peptides, polypeptides, proteins and oligonucleotides, which are entrapped by entrapping said substances in said hydrogel particles during formation thereof.

3. The hydrogel particles of claim 1, wherein in said process, said encapsulating is effected by sonication or hydrodynamic shear.

4. The hydrogel particles of claim 1, wherein said process of producing the same further comprises, after step b), adding an effective amount of a transport agent to the liquid medium in order to transport said calcium ions across the liposomal membranes to effect gelation of the hydrogel-forming substances.

5. The hydrogel particles of claim 1, wherein said liposomes are unilamellar liposomes.

6. The hydrogel particles of claim 1, wherein in said process, said calcium ions are obtained from calcium chloride.

7. The hydrogel particles of claim 1, wherein said liposomes are formed from a lipid material selected from the group selected from the group consisting of phosphatidyl ethers, phosphatidyl esters, phosphatidyl ethanolamine, phosphatidylcholine, glycerides, cerebrosides, gangliosides, sphingomyelin, steroids and cholesterol.

8. The hydrogel particles of claim 2, wherein said drugs are selected from the group consisting of antibiotics, anti-inflammatories, anti-neoplastics and cardiotonics.

9. The hydrogel particles of claim 2, wherein said vitamins are selected from the group consisting of vitamin C and vitamin E.

10. The hydrogel particles of claim 2, wherein said hormone is insulin.

* * * * *